United States Patent [19]

Itoh et al.

[11] Patent Number: 4,940,699

[45] Date of Patent: Jul. 10, 1990

[54] THIOPHOSPHORIC ACID ESTER AS A SOIL PEST CONTROLLING AGENT

[75] Inventors: Yoshikazu Itoh, Ibaraki; Makoto Hatakoshi, Toyonaka; Mitsuru Sasaki, Toyonaka, all of Japan

[73] Assignee: Sumitomo Chemical Company, Limited, Osaka, Japan

[21] Appl. No.: 344,409

[22] Filed: Apr. 28, 1989

Related U.S. Application Data

[63] Continuation-in-part of Ser. No. 258,761, Oct. 17, 1988, abandoned.

[30] Foreign Application Priority Data

Oct. 30, 1987 [JP] Japan .................. 62-276830

[51] Int. Cl.$^5$ ................ A01N 57/12; C07F 9/165
[52] U.S. Cl. ............................ 514/114; 558/7
[58] Field of Search ............... 558/7, 175; 514/114

[56] References Cited

U.S. PATENT DOCUMENTS

| | | | |
|---|---|---|---|
| 3,760,041 | 9/1973 | Lorenz et al. | 558/7 |
| 4,443,439 | 4/1984 | Ishikawa et al. | 558/7 |
| 4,473,562 | 9/1984 | King | 558/7 |

FOREIGN PATENT DOCUMENTS 52-33627  3/1977  Japan .
61-130203  6/1986  Japan .

*Primary Examiner*—Anton H. Sutto
*Attorney, Agent, or Firm*—Stevens, Davis, Miller & Mosher

[57] ABSTRACT

The present invention relates to an O,O-diethyl O-1-(N-methoxyimino)ethyl thiophosphonate and O,O-diethyl O-1-(N-methoxyimino)-propyl thiophosphate useful to control pests living in soil. Said compounds have an excellent activity in controlling pests living in soil such as southern corn rootworm, cupreous chafer etc.

6 Claims, No Drawings

THIOPHOSPHORIC ACID ESTER AS A SOIL PEST CONTROLLING AGENT

This is a continuation-in-part application of application Ser. No. 258,761, filed Oct. 17, 1988, now abandoned.

The present invention relates to a thiophosphoric acid ester, a process for producing the same and soil pest controlling agents containing the same as an active ingredient.

Hitherto, compounds having a closely related structure with the compound of the present invention have been disclosed in U.S. Pat. Nos. 3,760,041, 4,443,439 and 4,473,562, for example.

However, one can hardly say that the compounds described in the foregoing patents are satisfactory as an active ingredient for insecticides, particularly for soil pest controlling agents.

The present inventors have extensively studied to develop an effective controlling agent against the so-called soil pests living in soil and greatly damaging crops. As a result, they have found that the compounds having the formula (I) (hereinafter referred to as the present compound(s)),

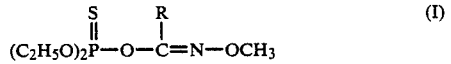

wherein R is a methyl or ethyl group, have an excellent efficacy.

The present compound is included in the scope encompassed by the general formula described in U.S. Pat. No. 4,473,562, but it contains neither exemplary disclosure nor suggestion on the present compound, and no description of test examples on soil pests either. The present inventors, however, confirmed that the present compound, as demonstrated later in the test examples, has an unexpectedly higher insecticidal activity against soil pests than do the known compounds having a closely related structure. The present inventors have thus attained to the present invention.

The present compound is produced, for example, by the process described below: O,O-diethyl thiophosphoric acid chloride having the formula (II),

is treated with N-methoxyacetamide or N-methoxypropionamide having the formula (III),

wherein R is described above, in a solvent in the presence of a base.

This process is usually carried out in the following reaction conditions.

In the reaction, the compound represented by the formula (III) is used in an amount of from 1 to 2 equivalents based on 1 equivalent of O,O-diethyl thiophosphoric acid chloride (II), and the base is used in an amount of from 1 to 2 equivalents based on the same.

The base includes for example inorganic bases (e.g. sodium hydride, potassium hydride, sodium hydroxide, potassium hydroxide, sodium carbonate, potassium carbonate), organic bases (e.g. pyridine, triethylamine), etc.

The reaction temperature and reaction time depend on the solvent used, but generally, they are from 0° to 100° C. and from 30 minutes to 24 hours, respectively.

The solvent includes for example aromatic hydrocarbons (e.g. toluene, benzene), ketones (e.g. methyl isobutyl ketone, methyl ethyl ketone, acetone), ethers (e.g. diethyl ether, tetrahydrofuran), acetonitrile, water and admixtures thereof.

After completion of the reaction, the desired present compound is obtained by the usual after-treatments such as extraction with organic solvents, etc. Also, the compound may be purified by column chromatography, etc. if necessary.

The present compound exhibits excellent efficacy against various soil pests, for example, pests of Diabrotica genus such as western corn rootworm (*Diabrotica virgifera* Le Conte), northern corn rootworm (*Diabrotica longicornis* Say), southern corn rootworm (*Diabrotica undecimpunctata howardi* Barber), etc.; pests of Anomala genus such as cupreous chafer (*Anomala cuprea* Hope), soybean beetle (*Anomala rufocuprea* Motschulsky), cherry chafer (*Anomala daimiana* Harlod), striated chafer (*Anomala testaceips* Motschulsky), etc.; pests of Popillia genus such as Japanese beetle (*Popillia japonica* Newman), etc.; pests of Aulacophora genus such as cucurbit leaf beetle (*Aulacophora femoralis* Motschulsky), etc.; pests of Phyllotreta genus such as stripped cabbage flea beetle (*Phyllotreta vittata* Fabricius), etc.; pests of Melanotus genus such as sweet potato wireworm (*Melanotus caudex* Lewis), etc.; pests of Agriotes genus such as barley wireworm (*Agriotes fuscicollis* Miwa), etc.; pests of Delia genus such as onion maggot (*Delia antiqua* Meigen), turnip maggot (*Delia floralis* Fallén), seed-corn maggot (*Delia platura* Meigen), etc.; pests of Gryllotalpa genus such as African mole cricket (*Gryllotalpa africana* Palisot de Beauvois), etc.; pests of Lissorhoptrus genus such as rice water weevil (*Lissorhoptrus oryzophilus* Kuschel), etc.; pests of Pratylenchus genus such as Cobb root-lesion nematode (*Pratylenchus penetrans* Cobb), walnut root-lesion nematode (*Pratylenchus vulnus* Allen et Jensen), coffee root-lesion nematode (*Pratylenchus coffeae* Zimmermann), etc.; pests of Heterodera genus such as soybean cyst nematode (*Heterodera glycines* Ichinohe), etc.; pests of Meloidogyne genus such as northern root-knot nematode (*Meloidogyne hapla* Chitwood), cotton root-knot nematode (*Meloidogyne incognita* var. *acrita* Chitwood), Javanese root-knot nematode (*Meloidogyne javanica* Treub), peanut root-knot nematode (*Meloidogyne arenaria* Neal), etc.; pests of Aphelenchoides genus such as rice white-tip nematode (*Aphelenchoides besseyi* Christie) and the like.

When the present compound is used as an active ingredient for soil pest controlling agents, it is usually formulated before use into oil sprays, emulsifiable concentrates, wettable powders, granules, dusts, aerosols, etc. by mixing with solid carriers, liquid carriers or gaseous carriers, and if necessary, adding surface active agents and/or other auxiliaries for formulation.

It is suitable that these preparations contain the present compound as an active ingredient in an amount of from 0.1 to 99.9% by weight, preferably from 1 to 80% by weight.

The solid carrier includes for example fine powders or granules of clays (e.g. kaolin clay, diatomite, synthetic hydrated silicon dioxide, bentonite, montmorillonite, terra alba), talcs, other inorganic minerals (e.g. attapulgite clay, sericite, quarts, sulfur, activated carbon, calcium carbonate, hydrated silica, pumice, zeolite), chemical fertilizers (e.g. ammonium sulfate, ammonium phosphate, ammonium nitrate, urea, ammonium chloride), etc. Of these carriers, oil-absorbing granular mineral carriers such as attapulgite clay, diatomite, bentonite, montmorillonite, pumice, zeolite, etc. are so easy to make formulations that they fit the economical production of impregnation-type granules.

The liquid carrier includes for example water, alcohols (e.g. methanol, ethanol), ketones (e.g. acetone, methyl ethyl ketone), aromatic hydrocarbons (e.g. benzene, toluene, xylene, ethylbenzene, methylnaphthalene), aliphatic hydrocarbons (e.g. hexane, cyclohexane, kerosene), esters (e.g. ethyl acetate, butyl acetate), nitriles (e.g. diisopropyl acetonitrile, isobutyronitrile), ethers (e.g. diisopropyl ether, dioxane), acid amides (e.g. dimethylformamide, dimethylacetamide), halogenated hydrocarbons (e.g. dichloroethane, trichloroethylene, carbon tetrachloride), etc.

The gaseous carrier, i.e. a propellant includes for example a freon gas, butane gas, carbon dioxide gas, etc.

The surface active agent includes for example alkyl sulfates, alkylsulfonates, alkylarylsulfonates, alkyl aryl ethers, polyhydric alcohol esters, sugar alcohol derivatives, etc.

The auxiliary for formulation such as fixing agents, dispersing agents, etc. includes for example casein, gelatin, polysaccharides (e.g. starch powder, gum arabic, cellulose derivatives, alginic acid), lignin derivatives, bentonite, saccharides, synthetic water-soluble high polymers (e.g. polyvinyl alcohol, polyvinyl pyrrolidone, polyacrylic acids), etc. The stabilizing agent includes PAP (isopropyl acid phosphate), BHT (2,6-di-tert-butyl-4-methylphenol), BHA (a mixture of 2-tert-butyl-4-methoxyphenol and 3-tert-butyl-4-methoxyphenol), vegetable oils, mineral oils, surface active agents, fatty acids and their esters, etc.

The formulation thus obtained are applied to soil surface as they are or diluted with water or the like. If necessary, they are mixed with soil after they have been applied to the soil surface, or they are drenched into soil. They can also be applied to foliage. Further, they may be used mixed with other insecticides, nematocides, acaricides, fungicides, herbicides, plant growth regulators, fertilizers or soil improvers, or may be used simultaneously with these chemicals without mixing.

When the present compound is used incorporated into soil pest controlling agents as an active ingredient, the application amount of the present compound is usually from 10 to 1000 g per 10 ares, preferably from 50 to 500 g per 10 ares. When the emulsifiable concentrates, wettable powders, etc. are used diluted with water, the application concentration of the active ingredient is from 0.01 to 30%, and the dusts, granules, oil sprays, aerosols, etc. are used as they are without being diluted.

Any of these application amount and concentration depends on the type of formulations, when, where and how these formulations are applied, the kind of pests, the degree of damage, etc., and it may be increased or decreased independently of the foregoing ranges.

The following production examples, formulation examples and test examples serve to give specific illustrations of the practice of the present invention but they are not intended to limit the scope of the present invention.

First, production examples for the present compound are shown below.

PRODUCTION EXAMPLE 1

2.35 Grams of N-methoxyacetamide were dissolved in 100 ml of acetonitrile. To this solution, 1.49 g of potassium hydroxide were added and the reaction mixture was kept at 50° C. To this reaction mixture, 5.0 g of O,O-diethyl thiophosphoric acid chloride were added and the mixture was refluxed for 5 hours. After removing acetonitrile, each 50 ml of benzene and water was added to the residue. The benzene residue was washed with water, dried over anhydrous magnesium sulfate, and the solvent was removed therefrom under reduced pressure, followed by purification with silica gel column chromatography to obtain 3.00 g of O,O-diethyl O-1-(N-methoxyimino)ethyl thiophosphate (the present compound (1)).

Refractive index: $n_D^{20.6}$ 1.4638

PRODUCTION EXAMPLE 2

1.59 Grams of 60% sodium hydride were suspended in 100 ml of tetrahydrofuran, and 4.1 g of N-methoxypropanamide were added by drops with stirring at room temperature. After completion of the addition, stirring was continued for further 1 hour, and 5.0 g of O,O-diethyl thiophosphoric acid chloride were added thereto by drops at room temperature. After completion of the addition, the mixture was heated under reflux for 3 hours. After the reaction had been completed, tetrahydrofuran was removed from the reaction mixture by evaporation, then 50 ml of methylene chloride and 50 ml of water were added to the resulting mixture to separate it into layers. The organic layer was washed with water and dried over anhydrous magnesium sulfate, and the solvent was removed therefrom under reduced pressure, followed by purification with silica gel column chromatography to obtain 4.59 g of O,O-diethyl O-1-(N-methoxyimino)propyl thiophosphate (the present compound (2)).

Refractive index: $n_D^{23.2}$ 1.4602

PRODUCTION EXAMPLE 3

4.31 Grams of potassium carbonate were suspended in 30 ml of methyl isobutyl ketone. With stirring at room temperature, 3.38 g of N-methoxypropanamide were added thereto by drops. After completion of the addition, stirring was continued for further 2 hours. Thereto were added 5.89 g of O,O-diethyl thiophosphoric acid chloride by drops at room temperature. After completion of the addition, the reaction mixture was heated under reflux for 2 hours. After the reaction had been completed, 50 ml of methylene chloride and 50 ml of water were added thereto to separate it into layers. The organic layer was washed with water and dried over anhydrous magnesium sulfate, and the solvent was removed therefrom under reduced pressure, followed by purification with silica gel column chromatography to obtain 3.38 g of the present compound (2).

Next, formulation examples are shown below: In the examples, parts are by weight.

FORMULATION EXAMPLE 1

Emulsifiable Concentrate

Forty parts of the present compound are dissolved in 50 parts of xylene, and 10 parts of an emulsifier, Sorpol SM-200 (a registered trade mark of Toho Chemical Industries Co., Ltd.; a mixture of polyoxyethylene alkylaryl ether, etc. and dodecylbenzenesulfonic acid), are added thereto. The resulting mixture is well stirred and mixed to obtain an emulsifiable concentrate having an active ingredient concentration of 40%.

FORMULATION EXAMPLE 2

Wettable Powder

Five parts of the foregoing emulsifier, Sorpol SM-200, are added to 40 parts of the present compound, and the mixture is well mixed. Thereafter, 20 parts of Carplex #80 (a registered trademark of Shionogi & Co., Ltd.; fine powders of synthetic hydrated silicon dioxide) and 35 parts of 300-mesh diatomite are added thereto. Then the resulting mixture is stirred and mixed on a juice mixer to obtain a wettable powder having an active ingredient concentration of 40%.

FORMULATION EXAMPLE 3

Granule

To 5 parts of the present compound are added 5 parts of Toyolignin CT (a registered trademark of Toyobo; lignin sulfonate) and 90 parts of GSM Clay (a registered trademark of Zieklite Mining Co., Ltd.; quartz powder). The resulting mixture is well stirred and mixed on a mixer. Subsequently, water is added to the mixture in an amount of 10% relative to the total amount of the mixture. The mixture is then further stirred, granulated on a granulator and air-dried to obtain a granule having an active ingredient concentration of 5%.

FORMULATION EXAMPLE 4

Dust

Five parts of the present compound are dissolved in 20 parts of acetone. To the resulting solution are added 3 parts of the foregoing Carplex #80, 0.3 part of PAP and 91.7 parts of 300-mesh talc. The mixture is stirred and mixed on a juice mixer. Removing acetone from the mixture by evaporation gives a dust having an active ingredient concentration of 5%.

FORMULATION EXAMPLE 5

Oil Spray

Twenty parts of the present compound are dissolved in 80 parts of kerosene to obtain an oil spray having an active ingredient concentration of 20%.

Next, the usefulness of the present compound as an active ingredient for soil pest controlling agents is demonstrated with reference to the following test examples. In the examples, compounds used as a control are shown by compound symbols in Table 1.

TABLE 1

| Compound symbol | Structural formula | Remarks |
|---|---|---|
| (A) | $C_2H_5O$-$\underset{\underset{C_6H_5}{\|}}{\overset{\overset{S}{\|}}{P}}$-$O$-$\underset{\underset{CH_3}{\|}}{C}$=$N$-$OCH_3$ | Compound described in U.S. Pat. No. 4,443,439 |
| (B) | $(C_2H_5O)_2\overset{\overset{S}{\|}}{P}$-$O$-$\underset{\underset{C_6H_5}{\|}}{C}$=$N$-$OCH_3$ | Compound described in U.S. Pat. No. 3,760,041 |
| (C) | $(C_2H_5O)_2\overset{\overset{S}{\|}}{P}$-$O$-$\underset{\underset{\triangle}{\|}}{C}$=$N$-$OCH_3$ | Compound described in U.S. Pat. No. 4,473,562 |
| (D) | $(C_2H_5O)_2\overset{\overset{S}{\|}}{P}$-$O$-$\underset{\underset{C_4H_9\text{-iso}}{\|}}{C}$=$N$-$OCH_3$ | Same as above |
| (E) | $(C_2H_5O)_2\overset{\overset{S}{\|}}{P}$-$O$-$\underset{\underset{CClH_2}{\|}}{C}$=$NOCH_3$ | Compound described in JP-A-52-33627 |

TEST EXAMPLE 1

Five milliliters of aqueous diluted solution of each of the emulsifiable concentrates obtained according to Formulation example 1 was mixed with 50 g of soil to give a soil samples having an active ingredient content in the soil of 0.5 or 0.25 ppm.

Each of these soil samples was filled in a polyethylene cup of 5.6 cm in diameter and 5.8 cm in height. In each cup, two corn grains having roots 2 to 3 cm long were planted and 10 third-instar larvae of southern corn rootworm (*Diabrotica undecimpunctata howardi* BARBER) were released. After two days, the number of the dead and alive larvae were counted for mortality (%). This test was repeated three times. Table 2 shows the results.

TABLE 2

| | Mortality (%) | |
|---|---|---|
| Test compound | 0.5 ppm | 0.25 ppm |
| Present compound (1) | 100 | 100 |
| Present compound (2) | 100 | 100 |
| (A) | 87 | 0 |
| (B) | 0 | — |
| (C) | 0 | — |
| (D) | 0 | — |
| (E) | 44 | 0 |

TEST EXAMPLE 2

Twenty milliliters of aqueous diluted solution of each of the emulsifiable concentrates obtained according to Formulation example 1 was mixed with 250-g soil/250-g sand mixture to give soil.sand mixture samples having an active ingredient content in the sample of 0.5 or 0.25 ppm. Each of these soil.sand mixture samples was filled in a polyethylene cup of 9 cm in diameter and 8 cm in height. Thereafter, 4 third-instar larvae of cupreous chafer (*Anomala cuprea* Hope) were released in each cup together with carrot disks (diameter, 3 cm; thickness, 5 mm). After 7 days, the number of the dead and alive larvae were counted for mortality (%) and percentage of moribund insects (%). This test was repeated twice. Table 3 shows the results. The percentage of dead insects plus moribund insects is shown in parenthesis.

TABLE 3

| Test compound | Mortality (%) [percentage of moribund insects (%)] | |
|---|---|---|
| | 0.5 ppm | 0.25 ppm |
| Present compound (2) | 100 | 100 |
| (A) | 0 | — |
| (C) | 0 [100] | 25 |

TEST EXAMPLE 3

Three parts of the present compound were admixed with 6 parts of polypropylene glycol (average molecular weight: 200). Then, the granular bentonite of Formulation example 6 was admixed therewith so as to make the whole 100 parts to impregnate the present compound into the carrier, whereby a granule containing 3% of the active ingredient was obtained. Thereafter, mixing this granule with 300 g of soil (16 mesh) gave a soil sample containing 2.5 ppm of the active ingredient. This soil sample was filled in a polyethylene cup of 9 cm in diameter and 8 cm in height and allowed to stand in a greenhouse. Three days after the treatment, 50 g of this soil sample were taken and filled in a polyethylene cup of 5.6 cm in diameter and 5.8 cm in height. Then, two corn grains having roots 2 to 3 cm long were planted and 10 third-instar larvae of southern corn rootworm (*Diabrotica undecimpunctata howardi* BARBER) of Test example 1 were released therein. Two days later, the dead and alive larvae were counted for mortality (%). This test was repeated three times. Table 4 shows the result.

TABLE 4

| Test compound | Mortality (%) |
|---|---|
| 3% Granule of the present compound (2) | 100 |

TEST EXAMPLE 4

With 7.5 parts of the present compound were admixed 8 parts of polypropylene glycol (average molecular weight: 200). Then, the granular bentonite (described above) was admixed therewith in a sufficient amount to make the whole 100 parts to impregnate the present compound into the carrier, whereby a granule containing 7.5% of the active ingredient was obtained. In the same manner as in Test example 9, the soil sample containing 2.5 ppm of the active ingredient was prepared and the activity against the southern corn rootworm (*Diabrotica undecimpunctata howardi* BARBER) of Test example 1 was examined. Table 5 shows the result.

TABLE 5

| Test compound | Mortality (%) |
|---|---|
| 7.5% Granules of the present compound (2) | 100 |

What is claimed is:

1. A soil pest controlling agent containing a compound of the formula (I),

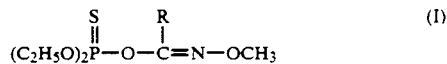

(I)

wherein R is a methyl or ethyl group, as an active ingredient.

2. The soil pest controlling agent according to claim 1, wherein R is a methyl group.

3. The soil pest controlling agent according to claim 1, wherein R is an ethyl group.

4. A compound of the formula (I),

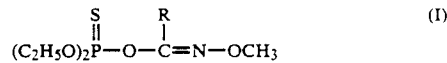

(I)

wherein R is a methyl or ethyl group.

5. The compound according to claim 4, wherein R is a methyl group.

6. The compound according to claim 4, wherein R is an ethyl group.

* * * * *